United States Patent [19]

Viehmann et al.

[11] Patent Number: 5,093,354

[45] Date of Patent: Mar. 3, 1992

[54] TOPICAL USE OF 2',4',6'-TRIMETHOXY-4-(1-PYRROLIDINYL) BUTYROPHENONE

[75] Inventors: Wolfgang Viehmann, Schwabmünchen; Thomas Högn, Cologne, both of Fed. Rep. of Germany

[73] Assignee: A. Nattermann & Cie Gmbh, Cologne, Fed. Rep. of Germany

[21] Appl. No.: 652,977

[22] Filed: Feb. 8, 1991

[30] Foreign Application Priority Data

Feb. 10, 1990 [DE] Fed. Rep. of Germany ....... 4004152
Nov. 27, 1990 [DE] Fed. Rep. of Germany ....... 4037658

[51] Int. Cl.$^5$ .............................................. A61K 31/40
[52] U.S. Cl. .................................... 514/428; 514/928
[58] Field of Search ................................. 514/428, 928

[56] References Cited

PUBLICATIONS

Chemical Abstracts 103:16247s (1985).

*Primary Examiner*—Leonard Schenkman
*Attorney, Agent, or Firm*—Herbert Dubno; Jonathan Myers

[57] ABSTRACT

A method of treating obstruction dermatoses, ulcus cruris, ulcus cruris venosum and decubital ulcers, is disclosed, which comprises topically treating an affected patient with a therapeutically effective amount of a pharmaceutical composition containing as active ingredient a therapeutically effective amount of 2',4',6'-trimethoxy-4-(1-pyrrolidinyl) butyrophenone or p-desmethyl-2', 4',6'-trimethoxy-4-(1-pyrrolidinyl) butyrophenone, or a pharmaceutically acceptable salt thereof.

7 Claims, No Drawings

TOPICAL USE OF 2',4',6'-TRIMETHOXY-4-(1-PYRROLIDINYL) BUTYROPHENONE

FIELD OF THE INVENTION

The present invention is directed to a novel use of 2', 4',6'-triemthoxy-4(1-pyrrolidinyl) butyrophenone, its salts and/or its derivatives for the manufacture of a pharmaceutical product.

BACKGROUND OF THE INVENTION

It is known to use 2',4',6'-trimethoxy-4-(1-pyrrolidinyl) butyrophenone in the form of its hydrochloride in pill form or as an injection solution for the treatment of peripheral arterial blood flow obstruction and diabetic angiopathy. This compound, also designated buflomedil, has the following structural formula:

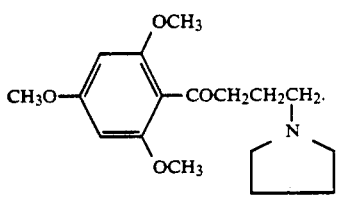

Trophic diseases are disturbances of the tissue or of the organs depending on nutrition and/or growth. The pains occurring in connection therewith, as for instance obstruction dermatoses or ulcus cruris venosum, are the most serious consequences of chronic venous insufficiency. These are caused by a constitutional weakness of the walls of the veins because of natural tendencies or as a result of thrombotic diseases. Furthermore, decubital ulcera are also trophic dermatic diseases; the decubital ulcera diseases appear to result from regional blood flow obstructions which occur especially often with immobilized patients confined to bed. This disease is even promoted by wetting of the corresponding surfaces of the skin with urine or sweat.

So, a study in Pharmakinetic 8 (6), 1986, pages 21 to 24 shows that about 2% of the population in the industrial states of the West have ulcera in leg regions of which about 90% have venous origins.

Up to now a standard therapy with drugs for the above-cited and described diseases, disturbances or pains, especially for the treatment of ulcus cruris venosum, decubital ulcera or obstruction dermatoses, has not existed. Only a symptomatic treatment is carried out without clear healing in many cases.

According to classical medicine the ulcus is cleaned and simultaneously treated antimicrobially and antiphlogistically. The cleaning of the ulcus can be carried out mechanically, osmotically or encymatically. Additionally, granulation-promoting and epithelizing agents can be used. By the application of surgical pressure dressings the venous afflux is simplified physically by keeping the patient in a state of rest is provided, as can be seen from Mörl, Fortschr. Med. 104 (21), 1986.

DESCRIPTION OF THE INVENTION

Surprisingly, it has been found that the above-described trophic diseases, the diseases resulting therefrom as well as the corresponding pains, especially obstruction dermatoses, ulcus cruris venosum and/or decubitalulcera, can be attended to with success if a pharmaceutical composition is used containing as active ingredient or as part of a combination of active ingredients 2',4',6'-trimethoxy-4-(1-pyrrolidinyl) butyrophenone, or a salt and/or derivative thereof. It has been observed that already after a very short application of such a pharmaceutical composition a permanent healing of these diseases or pains can be achieved. Especially with wet or wetting wounds caused by ulceration the same dried up after few treatments with the above-cited pharmaceutical product even if the product was a liquid application.

So, it could be observed that even after a short time, related to the customary duration of therapy, germinations into the vascular system from the depth of the ulcus as well as clearly recognizable isles of granulation occurred. Furthermore, the healing occurred by growth of the tissue not only from the depth of the ulcus but also from the edge so that previously required cosmetic after-treatments or corrections of the originally diseased regions were no more necessary. Furthermore, the application of antibiotics, sterilization agents and cleaning agents necessary in classical therapy for the fight against the additionally occurring bacterial infection could be significantly reduced.

Especially fast and pain-reducing therapy successes for the patient can be achieved if the used pharmaceutical product containing 2',4',6'-trimethoxy-4-(1-pyrrolidinyl) butyrophenone, salts and/or derivatives thereof as active ingredients is locally applied to the respective diseased areas. The pharmaceutical product can be used as liquid, semi-solid or solid medicine.

Liquid medicines are solutions, suspensions, emulsions or dispersions of the above-cited active ingredients or combinations of active ingredients as drops, tinctures and sprays. As semi-solid medicines, for example, gels, ointments, creams and foams are used while, for example, powders, toilet powders, granulates, pellets and microcapsules are used as solid medicines.

If the pharmaceutical product containing as active ingredient 2',4',6'-trimethoxy-4-(1-pyrrolidinyl) butyrophenone, salts and/or derivatives thereof is used as a liquid, it is recommended to use as far as possible irritation-free diluting agents, as for example water, monovalent alcohols, especially ethanol, polyvalent alcohols, especially glycerine and/or propanediol, polyglycols, especially polyethylene glycols and/or miglyols, glycerine formal, dimethylisosorbide, natural and synthetic oils and/or esters.

For the production of semi-solid products, as for example gels, ointments, creams and foams, in addition to the above-cited diluting agents basic materials, as for example bentonite, veegum, guar flour and/or cellulose derivatives, especially methylcellulose and/or caboxymethylcellulose, are suitable. Furthermore, instead of the above-cited basic materials or in addition to these materials polymers of vinylalcohol and vinylpyrrolidone, alginates, pectines, polyacrylates, solid and/or liquid polyethylenglycols, paraffins, fatty alcohols, vaseline and/or waxes, fatty acids and/or fatty acid esters are used. It is possible to use the above-cited active ingredients without filler for the production of solid products, as for example powders, toilet powder, granulates, pellets and microcapsules. The pharmaceutical product described here is especially suited for the attention of such of the above-described diseases which are in a very progressed stage so that at first an increased concentration of active ingredients is necessary. With less serious disease conditions or with progressive healing of the disease such embodiments of the solid pharmaceutical product are used which contain fillers, as for example colloidal silicic acid, powdered soapstone, milk sugar, starch powder, sugar, cellulose derivatives, gelatin, metal oxides and/or metal salts, wherein the concentration of the active ingredient or of the combination of active ingredients varies between 0.001% by weight and 50% by weight.

Furthermore, the above-described embodiments of the pharmaceutical product, dependent on the kind of dispensing means, can optionally contain further constituents, as for example conservation agents, stabilizing agents, tensides, emulsifiers, penetration promoters, spreading agents and/or ferments.

For the manufacture of the pharmaceutical product such additives are especially preferred which guarantee autosterility so that one can omit any additional conservation measures for the pharmaceutical product. Especially suited for this are such additives containing propylene glycol and/or glycerine, wherein these special additives preferably constitute more than 10% by weight of the pharmaceutical product. Furthermore, these additives have the advantage that they have a good compatibility, especially also dermal compatibility.

It is especially suitable if the pharmaceutical product manufactured in such a manner has a pH in a range of between 3.5 and 8, preferably of between 4.5 and 6.5. For example, this can be achieved by adding suitable buffer substances during the manufacture of the pharmaceutical product. With liquid or half-solid pharmaceutical products it is also possible to adjust the above-mentioned pH values by means of suitable acids or bases during their manufacture.

Furthermore, it can be necessary in the manufacture of the pharmaceutical product to add additionally antibiotics and/or sterilization agents. The concentration of the antibiotics varies in a range of between 5 mg and 300 mg, especially of between 50 mg and 200 mg, related to one g of the final pharmaceutical product, respectively. The addition of these antibiotics or sterilization agents promotes healing by preventing a secondary infection of the diseased areas which are treated. Furthermore, these antibiotics or sterilization agents guarantee that the products become sterile during the manufacture, filling or packing so that such a pharmaceutical product, especially in its liquid or half-solid embodiment, contains less than 1000, preferably less than 100, of non-pathogenic reproducing microorganisms per g.

For the manufacture of the pharmaceutical product the 2', 4',6'-trimethoxy-4-(1-pyrrolidinyl) butyrophenone indicated above by its structural formula is used. Instead of the 2',4',6'-trimethoxy-4-(1-pyrrolidinyl) butyrophenone or in addition to it salts, especially the corresponding hydrochloride, maleate and/or alkali and/or alkaline earth salts of the 2',4',6'-trimethoxy-4-(1-pyrrolidinyl) butyrophenone, which can be sulfated and/or sulfonated on the aromatic moiety and/or the pyrrolidine moiety, can be used for the manufacture of the pharmaceutical product. The pharmaceutical products which can be used for the treatment of the above-cited diseases, in addition to the above-cited active ingredients or instead of the above-cited ingredients, can contain derivatives, preferably pharmacologically active metabolic products (metabolites), of the 2',4',6'-trimethoxy-4-(1-pyrrolidinyl) butyrophenone, especially the p-desmethyl-2',4',6'-trimethoxy-4-(1-pyrrolidinyl) butyrophenone.

An especially suitable kind of pharmaceutical form of the above-described active ingredient is made by the application of the solid, liquid or semi-solid pharmaceutical product onto a gauze strip, a compress or a plaster so that such a gauze strip, such a compress or such a plaster then is only locally applied onto the spot which is to be treated.

As already described in connection with the solid form of the pharmaceutical product, the concentration of the active ingredients during the manufacture of the pharmaceutical product depends on the respective seriousness of the disease. Customarily, with solid medicine compositions the concentration of the active ingredient varies between 0.001% by weight and 100% by weight, and with liquid and half-solid medicine compositions between 0.01% by weight and 100% by weight, preferably between 1% by weight and 50% by weight. The difference with regard to 100% by weight results from the respective portion of the above-cited diluting agents and further additives.

The pharmaceutical product can be filled into the known receptacles, as for example bottles, tubes, toilet powder boxes and baby powder boxes as well as seal edge bags, which are possibly provided with metering means, as for example droplet forming means, metering valves or metering chambers.

SPECIFIC EXAMPLES

The inventive use is described in the following in detail by means of two examples.

EXAMPLE 1

A 50-years-old female patient having an ulcus cruris venosum for several years appeared to be at the end of the clinical therapy after treatment by means of customary therapy principles. The wound having a size of 0.4 cm had a discharge and was irritated, had a bad odor and was covered with greasy yellow coatings.

For the therapy the wound was cleaned with gentian violet or a gauze strip impregnated with 2',4',6'-trimethoxy-4-(1-pyrrolidinyl) butyrophenone-hydrochloride solution was directly applied to the wound in daily alternation. The concentration of the solution was 100 mg 2',4',6'-trimethoxy-4-(1-pyrrolidinyl) butyrophenone-hydrochloride in 10 ml NaCl solution. After three weeks the patient could leave the hospital with a healed ulcus cruris.

EXAMPLE 2

A female patient (56 years old) who appeared to be finished with her therapy and who had several ulcera cruris (0.2 to 6 cm) on her left foot or tibia for several years was treated in the following manner:

At the beginning a gauze strip impregnated with 2',4',6'-trimethoxy-4-(1-pyrrolidinyl) butyrophenone-hydrochloride solution (100 mg 2',4',6'-trimethoxy-4-(1-pyrrolidinyl) butyrophenone-hydrochloride in 10 ml NaCl solution) was directly applied to the cleaned wounds in a daily manner. After the beginning germination into the vascular system the therapy was carried out every of two days. After a therapy duration of three months the ulcera had been strongly diminished. A significantly covering tissue growth from the depth was recognizable.

We claim:

1. A method of treating obstruction dermatoses, ulcus cruris, ulcus cruris venosum and decubital ulcers, which comprises topically treating an affected patient with a therapeutically effective amount of a pharmaceutical composition containing as active ingredient a therapeutically effective amount of 2',4',6'-trimethoxy-4-(1-pyrrolidinyl) butyrophenone or p-desmethyl-2',4',6'-trimethoxy-4-(1-pyrrolidinyl) butyrophenone, or a pharmaceutically acceptable salt thereof.

2. The method defined in claim 1 wherein said pharmaceutical composition has a pH of 3.5 to 8.5.

3. The method defined in claim 2 wherein said pharmaceutical composition has a pH of 4.5 to 6.5.

4. The method defined in claim 3 wherein said pharmaceutical composition further comprises at least one antibiotic or sterilization agent.

5. The method defined in claim 4 wherein said pharmaceutical composition contains at least 10% by weight of at least one sterilization agent selected from the group which consists of propylene glycol or glycerine.

6. The method defined in claim 1 wherein the concentration of said 2',4',6'-trimethoxy-4-(1-pyrrolidinyl) butyrophenone or pharmaceutically acceptable salt thereof is between 1% and 50% by weight.

7. The method defined in claim 1 wherein said composition contains p-desmethyl-2',4',6'-trimethoxy-4-(1-pyrrolidinyl) butyrophenone as an active ingredient.

* * * * *

UNITED STATES PATENT AND TRADEMARK OFFICE
CERTIFICATE OF CORRECTION

PATENT NO. : 5,093,354
DATED : 3 March 1992
INVENTOR(S) : Wolfgang VIEHMANN et al It is certified that error appears in the above-indentified patent and that said Letters Patent is hereby corrected as shown below:

Col 1, line 8, for "4',6'-triemthoxy-4(1-pyrrolidinyl)" read -- 4',6'-trimethoxy-4(1-pyrrolidinyl) --;
Col. 1, lines 15 and 16, for "in pill form" read -- solid as tablets --;
Col. 1, line 31, for "pains" read -- complaints --;
Col. 1, lines 34 and 35, for "These are caused by a constitutional weakness of the walls of the veins because of natural tendencies" read -- These are caused by a predisposition due to a constitutional weakness of the walls of the veins --;
Col. 1, line 37, for "dermatic" read -- dermal --;
Col. 1, line 41, for "even" read -- further --;
Col. 1, line 43, for "Pharmakinetic" read -- Pharmacokinetics --;
Col. 1, line 47, for "therapy with drugs" read -- pharmacotherapy --;
Col. 1, line 49, for "pains" read -- complaints --;
Col. 1, line 56, for "encymatically" read -- enzymatically --;
Col. 1, line 59, for "afflux is simplified" read -- efflux is facilitated --;
Col. 1, line 60 for "ing the patient in a state of rest is provided, as can be" read -- ing the patient in a state of rest, as can be --;
Col. 1, line 66, for "pains" read -- complaints --;
Col. 2, line 5, for "application" read -- administration --;

UNITED STATES PATENT AND TRADEMARK OFFICE
CERTIFICATE OF CORRECTION

PATENT NO. : 5,093,354
DATED : 3 March 1992
INVENTOR(S) : Wolfgang Veihmann et al It is certified that error appears in the above-indentified patent and that said Letters Patent is hereby corrected as shown below:

```
Col. 2, line  7, for "pains" read -- complaints --;
Col. 2, line 23, for "the fight against" read -- control of --;
Col. 2, line 46, for "glycerine" read -- glycerol --;
Col. 2, line 48, for "glycerine" read -- glycerol --;
Col. 2, line 54, for "cabox-" read -- carbox --;
Col. 3, line 15, for "ferments" read -- propellants --;
Col. 3, line 21, for "glycerine" read -- glycerol --;
Col. 6, line  7, for "glycerine" read -- glycerol --; and
Col. 6, line 10, for "salt" read -- salts --.
```

Signed and Sealed this

Twelfth Day of July, 1994

BRUCE LEHMAN

Attest:

Attesting Officer

Commissioner of Patents and Trademarks ns
REEXAMINATION CERTIFICATE (2197th)

United States Patent [19]

Viehmann et al.

[11] B1 5,093,354

[45] Certificate Issued    Jan. 18, 1994

[54] TOPICAL USE OF 2',4',6'-TRIMETHOXY-4-(1-PYRROLINDINYL) BUTYROPHENONE

[75] Inventors: Wolfgang Viehmann, Schwabmünchen; Thomas Högn, Cologne, both of Fed. Rep. of Germany

[73] Assignee: A. Nattermann & Cie GmbH, Cologne, Fed. Rep. of Germany

Reexamination Request:
No. 90/003,107, Jun. 22, 1993

Reexamination Certificate for:
Patent No.:    5,093,354
Issued:        Mar. 3, 1992
Appl. No.:     652,977
Filed:         Feb. 8, 1991

[30]    Foreign Application Priority Data

Feb. 10, 1990 [DE]   Fed. Rep. of Germany ....... 4004152
Nov. 27, 1990 [DE]   Fed. Rep. of Germany ....... 4037658

[51] Int. Cl.$^5$ .............................................. A61K 31/40
[52] U.S. Cl. .................................... 514/428; 514/928
[58] Field of Search ............................. 514/428, 928

[56]          References Cited

FOREIGN PATENT DOCUMENTS

0369105  5/1990  European Pat. Off. .

OTHER PUBLICATIONS

Soins, No. 537, Jun. 1990, pp. 57 to 58, C. Gadenne-Tesse.
English Translation of the Soins Reference (1990).
Drugs 33, pp. 430 to 460 (1987).
Fortschritte Med. 103 (1-2) 1985, pp. 51-55.
English Translation of Fortschritte Reference (1985).
Z. Allg. Med. 61 (1-2) 1985, pp. 32-35.
English translation of the Z. Allg. Med. reference (1985).
Bernardini, A. Folha Medica, vol. 98, No. 4, pp. 247 to 251 (Apr. 1989).
English translation of Bernardini reference (1989).
Certified English Translation of German Patent Application P 40 04 152.2 (1991).

*Primary Examiner*—Frederick E. Waddell

[57]          ABSTRACT

A method of treating obstruction dermatoses, ulcus cruris, ulcus cruris venosum and decubital ulcers, is disclosed, which comprises topically treating an affected patient with a therapeutically effective amount of a pharmaceutical composition containing as active ingredient a therapeutically effective amount of 2',4',6'-trimethoxy-4-(1-pyrrolidinyl) butyrophenone or p-desmethyl-2', 4',6'-trimethoxy-4-(1-pyrrolidinyl) butyrophenone, or a pharmaceutically acceptable salt thereof.

REEXAMINATION CERTIFICATE ISSUED UNDER 35 U.S.C. 307

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 1, lines 7–10:

The present invention is directed to a novel use of [2',4',6'-trimethoxy-4(1-pyrrolidinyl) butyrophenone] *2',4',6'-trimethoxy-4(1-pyrrolidinyl) butyrophenone*, its salts and/or its derivatives for the manufacture of a pharmaceutical product.

Column 1, lines 13–18:

It is known to use 2',4',6'-trimethoxy-4(1-pyrrolidinyl) butyrophenone in the form of its hydrochloride [in pill form] *solid as tablets* or as an injection solution for the treatment of peripheral arterial blood flow obstruction and diabetic angiopathy. This compound, also designated buflomedil, has the following structural formula:

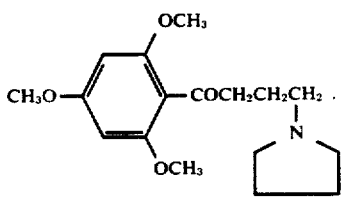

Column 1, lines 29–42:

Trophic diseases are disturbances of the tissue or of the organs depending on nutrition and/or growth. The [pains] *complaints* occurring in connection therewith, as for instance obstruction dermatoses or ulcus cruris venosum, are the most serious consequences of chronic venous insufficiency. [These are caused by a constitutional weakness of the walls of the veins because of natural tendencies or] *These are caused by a predisposition due to a constitutional weakness of the walls of the veins* as a result of thrombotic diseases. Furthermore, decubital ulcera are also trophic [dermatic] *dermal* diseases; the decubital ulcera diseases appear to result from regional blood flow obstructions which occur especially often with immobilized patients confined to bed. This disease is [even] *further* promoted by wetting of the corresponding surfaces of the skin with urine or sweat.

Column 1, lines 43–46:

So, a study in [Pharmakinetic 8 (6)] *Pharmacokinetics 8 (6)*, 1986, pages 21 to 24 shows that about 2% of the population in the industrial states of the West have ulcera in leg regions of which about 90% have venous origins.

Column 1, lines 47–52:

Up to now a standard [therapy with drugs] *pharmacotherapy* for the above-cited and described diseases, disturbances or [pains] *complaints*, especially for the treatment of ulcus cruris venosum, decubital ulcera or obstruction dermatoses, has not existed. Only a symptomatic treatment is carried out without clear healing in many cases.

Column 1, lines 53–61:

According to classical medicine the ulcus is cleaned and simultaneously treated antimicrobially and antiphlogistically. The cleaning of the ulcus can be carried out mechanically, osmotically or [encymatically] *enzymatically*. Additionally, granulation-promoting and epithelizing agents can be used. By the application of surgical pressure dressings the venous [afflux is simplified] *afflux is facilitated* physically by keeping the patient in a state of rest [is provided] as can be seen from Mörl, Fortschr. Med. 104(21), 1986.

Column 1, line 64 to Column 2, line 11:

Surprisingly, it has been found that the above-described trophic diseases, the diseases resulting therefrom as well as the corresponding [pains] *complaints*, especially obstruction dermatoses, ulcus cruris, venosum and/or decubitalulcera, can be attended to with success if a pharmaceutical composition is used containing as active ingredient or as part of a combination of active ingredients 2',4',6'-trimethoxy-4-(1-pyrrolidinyl) butyrophenone, or a salt and/or derivative thereof. It has been observed that already after a very short [application] *administration* of such a pharmaceutical composition a permanent healing of these diseases or [pains] *complaints* can be achieved. Especially with wet or wetting wounds caused by ulceration the same dried up after few treatments with the above-cited pharmaceutical product even if the product was a liquid application.

Column 2, lines 12–25:

So, it could be observed that even after a short time, related to the customary duration of therapy, germinations into the vascular system from the depth of the ulcus as well as clearly recognizable isles of granulation occurred. Furthermore, the healing occurred by growth of the tissue not only from the depth of the ulcus but also from the edge so that previously required cosmetic after-treatments or corrections of the originally diseased regions were no [more] *longer* necessary. Furthermore, the application of antibiotics, sterilization agents and cleaning agents necessary in classical therapy for [the fight against] *control of* the additionally occurring bacterial infection could be significantly reduced.

Column 2, lines 40–49:

If the pharmaceutical product containing as active ingredient 2',4',6'-trimethoxy-4-(1-pyrrolidinyl) butyrophenone, salts and/or derivatives thereof is used as a liquid, it is recommended to use as far as possible irritation-free diluting agents, as for example water, monovalent alcohols, especially ethanol, polyvalent alcohols, especially [glycerine] *glycerol* and/or propanediol, polyglycols, especially polyethylene glycols and/or miglyols, [glycerine] *glycerol* formal, dimethylisosorbide, natural and synthetic oils and/or esters.

Column 2, line 50 to Column 3, line 9:

For the production of semi-solid products, as for example gels, ointments, creams and foams, in addition to the above-cited diluting agents basic materials, as for example bentonite, veegum, guar flour and/or cellulose derivatives, especially methylcellulose and/or [caboxymethylcellulose] *carboxymethycellulose*, are suitable. Furthermore, instead of the above-cited basic materials or in addition to these materials polymers of vinylalcohol and vinylpyrrolidone, alginates, pectines, polyacrylates, solid and/or liquid polyethylenglycols, paraffins, fatty alcohols, vaseline and/or waxes, fatty acids and/or fatty acid esters are used. It is possible to use the above-cited active ingredients without filler for the production of solid products, as for example powders, toilet powder, granulates, pellets and microcapsules. The pharmaceutical product described here is especially suited for the attention of such of the above-described diseases which are in a very progressed stage so that at first an increased concentration of active ingredients is necessary. With less serious disease conditions or with progressive healing of the disease such embodiments of the solid pharmaceutical product are used which contain fillers, as for example colloidal silicic acid, powdered soapstone, milk sugar, starch powder, sugar, cellulose derivatives, gelatin, metal oxides and/or metal salts, wherein the concentration of the active ingredient or of the combination of active ingredients varies between 0.001% by weight and 50% by weight.

Column 3, lines 10–15:

Furthermore, the above-described embodiments of the pharmaceutical product, dependent on the kind of dispensing means, can optionally contain further constituents, as for example conservation agents, stabilizing agents, tensides, emulsifiers, penetration promoters, spreading agents, and/or [ferments] *propellants.*

Column 3, lines 16–26:

For the manufacture of the pharmaceutical product such additives are especially preferred which guarantee autosterility so that one can omit any additional conservation measures for the pharmaceutical product. Especially suited for this are such additives containing propylene glycol and/or [glycerine] *glycerol*, wherein these special additives preferably constitute more than 10% by weight of the pharmaceutical product. Furthermore, these additives have the advantage that they have a good compatibility, especially also dermal compatibility.

AS A RESULT OF REEXAMINATION, IT HAS BEEN DETERMINED THAT:

The patentability of claims 1, 3 and 7 is confirmed.

Claims 4 and 6 are cancelled.

Claims 2 and 5 are determined to be patentable as amended.

2. The method defined in claim 1 wherein said pharmaceutical composition has a pH of 3.5 to [8.5] *8*.

5. The method defined in claim [4] *1* wherein said pharmaceutical composition contains at least 10% by weight of at least one sterilization agent selected from the group which consists of propylene glycol or glycerine.

* * * * *